(12) United States Patent
Young

(10) Patent No.: US 8,846,087 B2
(45) Date of Patent: Sep. 30, 2014

(54) FORMULATION FOR PROVIDING AN ENTERIC COATING MATERIAL

(75) Inventor: Vic Young, West Lothian (GB)

(73) Assignee: Sensient Colors LLC, St. Louis, MO (US)

(*) Notice: Subject to any disclaimer, the term of this patent is extended or adjusted under 35 U.S.C. 154(b) by 2256 days.

(21) Appl. No.: 10/569,798

(22) PCT Filed: Aug. 25, 2004

(86) PCT No.: PCT/GB2004/003623
§ 371 (c)(1),
(2), (4) Date: Nov. 14, 2006

(87) PCT Pub. No.: WO2005/020708
PCT Pub. Date: Mar. 10, 2005

(65) Prior Publication Data
US 2007/0071821 A1    Mar. 29, 2007

(30) Foreign Application Priority Data
Aug. 27, 2003   (GB) .................................. 0320020.1

(51) Int. Cl.
*A61K 9/28*   (2006.01)
*A23L 1/00*   (2006.01)
*A61K 9/48*   (2006.01)

(52) U.S. Cl.
CPC ............... *A61K 9/286* (2013.01); *A61K 9/288* (2013.01); *A61K 9/282* (2013.01); *A61K 9/4891* (2013.01); *A23L 1/0052* (2013.01)
USPC ........... 424/474; 424/417; 424/475; 424/479; 424/490

(58) Field of Classification Search
CPC .............................. A61K 9/08; A61K 9/2806
USPC ......... 424/414, 417–420, 474, 468, 475, 490, 424/496–499
See application file for complete search history.

(56) References Cited

U.S. PATENT DOCUMENTS

| | | | |
|---|---|---|---|
| 3,126,320 A | | 3/1964 | Blue |
| 3,350,329 A | * | 10/1967 | Scholl .............................. 524/25 |
| 4,769,168 A | | 9/1988 | Ouhadi et al. |
| 4,778,479 A | * | 10/1988 | Romling et al. ............. 29/623.1 |
| 4,778,749 A | * | 10/1988 | Vasington et al. ................ 435/2 |
| 4,973,469 A | | 11/1990 | Mulligan et al. |
| 5,128,142 A | | 7/1992 | Mulligan et al. |
| 5,567,438 A | * | 10/1996 | Cook ............................ 424/474 |
| 6,083,532 A | * | 7/2000 | Zhang et al. ................... 424/468 |
| 6,326,028 B1 | * | 12/2001 | Nivaggioli et al. ........... 424/481 |
| 6,365,148 B1 | * | 4/2002 | Kim et al. ..................... 424/93.1 |
| 6,620,431 B1 | | 9/2003 | Signorino |
| 2011/0002986 A1 | | 1/2011 | Durig et al. |

FOREIGN PATENT DOCUMENTS

| | | |
|---|---|---|
| DE | 2328409 | 6/1973 |
| DE | 3625189 A1 | 2/1987 |
| DE | 19907764 | 2/1999 |
| EP | 0120659 B1 | 7/1990 |
| EP | 1056345 B1 | 7/2002 |
| GB | 1415210 | 11/1975 |
| JP | 2002-193831 | 10/2002 |
| WO | 02/085304 | 10/2002 |
| WO | WO 02/085304 | 10/2002 |
| WO | 03/057233 | 7/2003 |
| WO | WO 03/057233 | 7/2003 |

OTHER PUBLICATIONS

Communication dated Mar. 28, 2012 in European Opposition of EP Application No. EP1667533.
Communication dated Nov. 27, 2012 in European Opposition of EP Application No. EP1667533.
Communication dated Jun. 28, 2013 in European Opposition of EP Application No. EP 1667533.
Communiation dated Jul. 4, 2013 in European Opposition of EP Application No. EP 1667533.
Journal of Applied Chemistry of the USSR, 50(4), pp. 697-702, Sep. 20, 1977.
European Opposition of Evonik Rohm GmbH, Sep. 28, 2010.
English Language Translation of selected portions of the European Opposition of Evonik Rohm GmbH, Sep. 29, 2010.
European Opposition of Hercules Incorporated, Sep. 29, 2010.
Response to European Opposition of MW Encap Limited, May 16, 2011.
*Shellac Algin*, Journal of the Society of Chemical Industry, Apr. 29, 1886, p. 221.
W.A. Ritschel et al., *Die Tablette*, Editio Cantor Verlag Aulendorp, $2^{nd}$ Edition, 2002, pp. 30-32, 583-586.
E. Pandula et al., *Effect of Additives on the Solubility of Protective Film Coatings*, Acta Pharmaceutica Hungarica, vol. 41, 1971, pp. 58-62, and English Language Translation.
Definition of "Enteric Coating," Mosby's Dental Dictionary, $2^{nd}$ Ed., 2008.
Description of Shellac, Handbook of Pharmaceutical Excipients, $3^{rd}$ Edition, 2000.

* cited by examiner

*Primary Examiner* — Michael G Hartley
*Assistant Examiner* — Micah-Paul Young
(74) *Attorney, Agent, or Firm* — Whyte Hirschboeck Dudek S.C.

(57) ABSTRACT

The present invention relates to an enteric coating formulation, as well as methods for preparing and using said enteric coating formulation. In particular, the invention relates to an enteric coating formulation that is made up of foodeous approved materials.

11 Claims, No Drawings

FORMULATION FOR PROVIDING AN ENTERIC COATING MATERIAL

This application is a U.S. National Phase of International Application No. PCT/GB2004/003623, filed Aug. 25, 2004, which claims priority to Great Britain Patent Application No. 0320020.1, filed on Aug. 27, 2003, the entire contents of each of which are hereby incorporated by reference.

The present invention relates to a formulation for providing an enteric coating material and in particular relates to such a material made up of food use approved materials.

In many cases it is a requirement of pharmaceutical and neutraceutical dosage units that they are able to pass through the stomach intact and only release their contents further down the GI Tract. This is necessary when a particular ingredient (or ingredients) of the dosage unit is unstable in the strongly acidic environment of the stomach and where the ingredient or ingredients are intended for release in the slightly alkaline conditions of the GI Tract beyond the stomach.

The prior art shows many cases where pharmaceutical dosage units achieve the abovementioned requirement using an enteric coating. Enteric coating materials are material types that are acid resistant, protecting and preventing the dosage unit from a releasing of the contents into the stomach. However, these coatings dissolve or disintegrate in the neutral or mildly alkaline conditions that are encountered beyond the stomach. In the pharmaceutical industry enteric coatings are widely used, with a wide choice of enteric materials such as hydroxypropyl methylcellulose phthalate (HPMCP), methacrylic acid/methyl methacrylate copolymers (for example Eudragit™ materials), cellulose acetate pthalate (cap) and polyvinyl acetate phthalate (PVAP). All of these enteric materials have been developed over a considerable period to provide a wide range of organic solvent soluble materials or aqueous dispersions that have both excellent coating and enteric properties. However, manufacturers have had to invest heavily to gain approval for the use of their materials in the pharmaceutical industry and rigorous testing of the materials has been required. Although all of these products have been through this pharmaceutical approval route, they have not been considered as viable propositions for companies to devote similar significant resources to gain approval for use in the food industry. Therefore, although these materials are appropriate enteric materials they are not approved for food use and cannot legally be used to provide enteric coatings for non-pharmaceutical dosage units. There are many cases when it would be useful to provide enteric coatings on items that are non-pharmaceutical dosage units, for example for certain health foods etc.

There are in fact very few materials that are both approved for food use and can be used as enteric coatings. An example of a material that is approved for food use and has been used or suggested as a enteric coating material is Zein. Zein is a prolamine obtained from corn and is used as a tablet binder or tablet coating agent. It has in the past been used as an enteric coating material and is insoluble in water and most of the common organic solvents including both acetone and ethanol. It can be dissolved and sprayed as a film from propylene glycol/water solutions but due to the high propylene glycol content (typically over 75%) and high boiling point of propylene glycol, its use suffers from technical, solution cost and environmental consideration problems. Zein coats form a very weak film in acid which, in tests, fail to resist 0.1 N HCl for two hours. The coating does not dissolve in neutral or mildly alkaline conditions and therefore does not perform as a satisfactory enteric coating material. It again has been suggested that the Zein coat is digested rather than dissolved in the intestine, which is a rather unusual, and non-enteric, release mechanism. Therefore Zein is not particularly useful as an enteric non-pharmaceutical coating.

Another possible material that has been suggested is Shellac. Shellac is an exudate of the lac insect and is a natural material that is insoluble in water but soluble in organic solvents including ethanol. The term shellac covers the range of this type of material. It has been used as a sealing coat on tablet cores, as a food glaze and also as a type on enteric coating. As Shellac is insoluble in acidic conditions but soluble at higher pH levels it would appear to be suitable as an enteric coating material. However, reference texts describe that, in practice, delayed disintegration and delayed drug release occurs in vivo as the Shellac coat is not soluble in the upper intestine. Laboratory trials in this case have now shown that Shellac does not behave in a typical enteric coating manner and instead behaves more like an erodable coating, dissolving as a function of time rather than of pH.

Traditionally, Shellac coats have been sprayed from an organic solution, a disadvantage in terms of solution cost and environmental protection cost. It is possible to spray Shellac from an aqueous solution after forming the Shellac into a water soluble alkali salt, and aqueous Shellac salt solutions are commercially available. These commercially available solutions form films that dissolve in neutral or mildly alkaline conditions and appear, at first consideration, to overcome the alkaline insolubility problem of Shellac sprayed from organic solution. However, unfortunately these films react rapidly in acid to revert to the free acid Shellac and, when ingested as a film of a dosage unit, the acidic conditions in the stomach restore the film to Shellac and restore the insolubility problem. Shellac films sprayed as Shellac or as Shellac salts perform similarly and neither resists acid (0.1H NCl for two hours) and rapidly (within one hour) releases the contents of the dosage unit in neutral or mildly alkaline conditions in the manner of an enteric coat. Shellac films can be produced that disintegrate between two and three hours and would appear to meet the above requirements. However Shellac films are relatively insensitive to pH and, as described above, disintegrate between two and three hours regardless of the solution acidity or alkalinity and instead behave as erodable films which dissolve as a function of time.

It can be seen that it would be beneficial to provide an enteric coating material that overcomes the problems of the prior art.

It is an object of the present invention to provide an enteric coating material.

According to a first aspect of the present invention there is provided an enteric coating formulation comprising shellac and alginate.

Preferably the alginate is sodium alginate.
Preferably the Shellac is in aqueous form.
Most preferably, the Shellac is in aqueous salt form.
Preferably the formulation is edible.
Most preferably the formulation comprises materials that are approved for food use.
Optionally, the formulation comprises between 10-90% Shellac.
Optionally, the formulation comprises between 10-90% alginate.
Preferably, the formulation comprises equal quantities of Shellac and alginate.
Preferably, the formulation is in the form of a spray solution or a suspension.
Preferably, a low viscosity grade of alginate is used.

Preferably, the alginate has a viscosity of between 200 and 300 cps.

Optionally, a plasticiser may be added to the formulation.

According to a second aspect of the present invention there is provided a method of applying an enteric coating formulation of the type described in the first aspect wherein the formulation is applied to a dosage unit as a spray.

Optionally, the pH of the formulation may be adjusted to maintain a useable solution/suspension.

Optionally, the pH of any of the components of the formulation may be adjusted to maintain a useable solution/suspension.

According to a third aspect of the present invention there is provided a dosage unit comprising enteric outer coating which is itself comprises Shellac and alginate.

Preferably the alginate is sodium alginate.

According to a fourth aspect of the present invention there is provided a method for preparing an enteric coating comprising the steps mixing an aqueous solution of an alkali salt of Shellac with an aqueous solution of sodium alginate.

In order to provide a better understanding of the present invention the invention will be described by way of example only and with reference to the following drawing in which FIG. 1 shows a cross section of a dosage unit comprising an enteric coating according to the present invention.

Sodium alginate is GRAS listed and recognised as a food additive in Europe. It is used as a stabilising agent, suspending agent, tablet and capsule disintegrant, tablet binder and viscosity increasing agent. However, until now it has never been suggested as a constituent of an enteric coating material. It is described in the art as being insoluble below pH3 and slowly soluble in neutral or alkaline solution and forms aqueous solutions. Therefore it would not appear obvious to use sodium alginate as part of an enteric coating.

Neither Shellac, in free acid or alkaline salt form, nor sodium alginate form films that are acid resistant (where an acid is 0.1 N HCl) and dissolve or disintegrate in neutral/mildly alkaline conditions (i.e. pH 6.8 buffer), i.e. neither performs the function of an enteric coat.

In the preferred embodiment of the present invention, Shellac, in the aqueous salt form, and sodium alginate are be mixed together to provide a formulation which forms a film that resists acid but disintegrates in neutral/mildly alkaline conditions. This film has the properties of an enteric film and is entirely composed of food use acceptable materials. Therefore, it is usable by the food and neutraceutical industry to coat non-pharmaceutical (i.e. non-licensed) dosage units where an enteric coating may still be of great use.

In alternative embodiments, alginic acid, other salts of alginic acid (alginates) or alginic acid derivatives such as potassium alginate could be used in place of sodium alginate.

As a preliminary step Shellac may be formed into a solution of the alkali salt using standard techniques known in the art. An example of such a technique is to heat Shellac in water, with stirring, to 50-55° C. then, after dissolution of the Shellac and the addition of 10% solution of ammonium hydrogen carbonate, the mixture is heated to 60° C., with stirring for a further 30 minutes. On cooling, the Shellac remains in solution as the alkali salt.

The coating formulation is formed by mixing an aqueous solution and of an alkali salt of Shellac with an aqueous solution of sodium alginate. The content of either material may vary from 10% of one to 90% and will still demonstrate enteric properties in the film formed. Most preferably the constituents are present in equal quantities. The pH of the mixture, or either component within the mixture, may be adjusted and selected to maintain a useable solution or suspension.

The aqueous solution of the alkali Shellac salt may be formed from Shellac as part of the preliminary process using methods known in the art.

It is also worth noting that sodium alginate is commercially available as different grades which form solutions of wildly different viscosities. Preferably, in this case, a low viscosity grade of sodium alginate will be used. The preferred viscosity of the sodium alginate is 200-300 cps (centipoise), defined as a viscosity of a 3% solution in water with a sequestering agent.

A plasticiser may be added to the formulation to modify the flexibility of the film formed to suit the dosage requirements. Examples of plasticisers are triethylcitrate, polyethylene glycol, polypropylene glycol and glycerin monostearate. The plasticisers would typically be added in the 5-25% range. The aqueous Shellac/sodium alginate solution or suspension can, at suitable concentration which is spraying system dependent, be sprayed using commercial equipment by personnel skilled in the art to form films on dosage units.

It can be seen that the present invention has a number of benefits over the prior art and up until now this combination of materials has not been known to produce a film that has enteric properties and is acceptable for food use. As none of the materials themselves perform in an enteric manner it is somewhat surprising to find that the combination of material produces a film that shows enteric properties, a property possessed by neither of the components.

It should be noted that the embodiments disclosed above are merely exemplary of the invention which may be embodied in many different forms. Therefore, details disclosed herein are not to be interpreted as limiting but merely as a basis for claims and for teaching one skills in the art as to the various uses of the present invention in any appropriate manner.

The invention claimed is:

1. An enteric coating formulation comprising a mixture of an aqueous solution of shellac salt and an aqueous solution of alginate, wherein the formulation comprises between 10-90% aqueous solution of shellac salt and between 10-90% aqueous solution of alginate.

2. The enteric coating formulation as in claim 1, wherein the alginate is sodium alginate.

3. The enteric coating formulation as in claim 1, wherein the formulation is edible.

4. The enteric coating formulation as in claim 1, where there are equal quantities of shellac salt and alginate present in the formulation.

5. The enteric coating formulation as in claim 1, wherein the formulation is in the form of a spray solution or a suspension.

6. The enteric coating formulation as in claim 1, wherein the alginate is of a low viscosity grade.

7. The enteric coating formulation as in claim 1, wherein the alginate has a viscosity of between 200 and 300 cps.

8. The enteric coating formulation as in claim 1, wherein the formulation further comprises a plasticiser.

9. A method of applying the enteric coating formulation of claim 1, wherein the formulation is applied to a dosage unit by spraying.

10. A dosage unit comprising an enteric outer coating, wherein the enteric outer coating is of a formulation as described in claim 1.

11. A method for preparing the enteric coating of claim 1, comprising the step of mixing an aqueous solution of an alkali salt of shellac with an aqueous solution of sodium alginate.

\* \* \* \* \*